United States Patent [19]
Connor et al.

[11] 4,016,257
[45] Apr. 5, 1977

[54] AMIDE DERIVATIVES OF ACIDS, AN ANTIBIOTIC PRODUCED BY *POLYANGIUM CELLULOSUM* VAR. *FULVUM*

[75] Inventors: David T. Connor, Parsippany; Samuel M. Ringel, Rockaway; Maximilian von Strandtmann, Rockaway Township, Morris County, all of N.J.

[73] Assignee: Warner-Lambert Company, Morris Plains, N.J.

[22] Filed: Aug. 7, 1975

[21] Appl. No.: 602,844

[52] U.S. Cl. ............................................. 424/122
[51] Int. Cl.$^2$ ...................................... A61K 35/74
[58] Field of Search ..................................... 424/122

[56] References Cited

UNITED STATES PATENTS 3,804,948  4/1974  Strandtmann et al. ............ 424/122

*Primary Examiner*—Jerome D. Goldberg
*Attorney, Agent, or Firm*—Albert H. Graddis; Frank S. Chow; Anne M. Kelly

[57] ABSTRACT

The present invention relates to cyclic and acyclic amide derivatives of the antibiotic substance, designated acid S, produced by *Polyangium cellulosum* var. *fulvum* (ATTC No. 25532), to the acetates thereof and to processes for the production of the amides and their corresponding diacetates. The amide derivatives of acid S of this invention are useful as antifungal and antibacterial agents.

5 Claims, 5 Drawing Figures

ACID S (N-BUTYLAMINE) AMIDE

ACID S (BENZYLAMINE) AMIDE

ACID S (PIPERIDINE) AMIDE

ACID S (PYRROLIDINE) AMIDE

AMIDE DERIVATIVES OF ACIDS, AN ANTIBIOTIC PRODUCED BY *POLYANGIUM CELLULOSUM* VAR. *FULVUM*

SUMMARY OF THE INVENTION

The present invention relates to novel cyclic and acyclic amides obtained by structurally modifying substance known as acid S, a potent antibiotic isolated from Polyangium cellulosum var. fulvum (ATCC No. 25532). Specifically, the present invention relates to amide derivatives of acid S having the formula I or II:

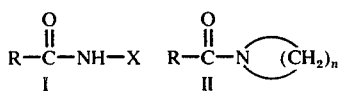

wherein X in formula I is alkyl, aralkyl or cycloalkyl, wherein alkyl is a 1 to 7 carbon lower alkyl and aryl is phenyl or naphthyl; and $n$ in formula II is any number from 3 to 8. Preferably, X in formula I is 1 to 4 carbon lower alkyl or benzyl; and $n$ in formula II is 4 or 5. R in formula I and II is the neutral part of the acid S molecule and has the empirical formula $C_{27}H_{41}O_4$. The acid S molecule has the formula $R-CO_2H$ ($C_{28}H_{42}O_6$).

The cyclic and acyclic amide derivatives of acid S formed according to the process of this invention may be acetylated to determine the number of secondary hydroxyl groups present in each of the structural modifications. By means of this acetylation reaction, it was found that, in each case, the corresponding diacetate is formed indicating the presence of two hydroxyl groups.

BRIEF DESCRIPTION OF THE DRAWINGS

The infrared spectra of representative cyclic and acyclic derivative of acid S of this invention are illustrated in FIGS. 1, 2, 3, 4 and 5 of the drawings.

Figure 1:
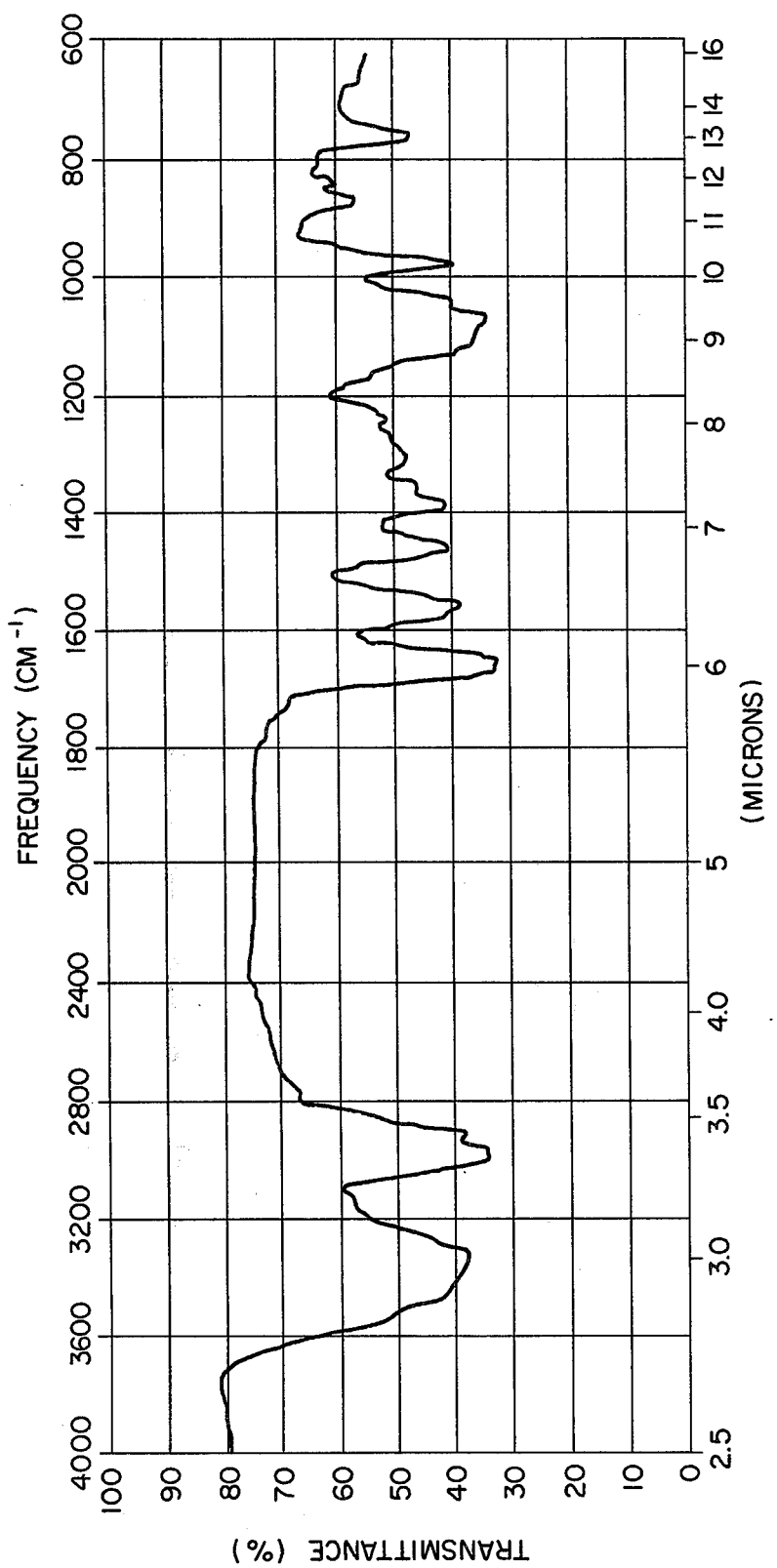
FIG. 1 depicts the infrared spectrum of acid S(n-butylamine)amide.

The novel amide derivatives of acid S of this invention are prepared from the antibiotic acid S and its corresponding methyl ester. Acid S, as disclosed in U.S. Pat. No. 3,651,216, issued Mar. 21, 1972 and in U.S. Pat. No. 3,804,948, issued Apr. 16, 1974, is a potent antifungal substance, elaborated when the microorganism *Polyangium cellulosum* var. *fulvum* (ATCC N0. 25532) is fermented in a suitable culture medium. The aforementioned U.S. Pat. No. 3,804,948 also describes the chemical preparation of the methyl ester of acid S.

The organism designated *Polyangium cellulosum* var. *fulvum* is deposited at the American Type Culture Collection, and identified as ATCC No. 25532. All restriction on the availability of the culture deposit at ATCC will be irrevocably removed upon issuance of the instant application. The culture at ATCC will be maintained throughout the effective life of the patent.

Thus, according to this invention one equivalent of acid S methyl ester ($C_{29}H_{44}O_6$) is reacted with an excess of an amine selected from the group $XNH_2$ or

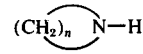

wherein X is lower alkyl, aralkyl or cycloalkyl, wherein alkyl is a 1 to 7 carbon lower alkyl and aryl is phenyl or naphthyl; and $n$ is a number from 3 to 8. Preferably, X is a 1 to 4 carbon lower alkyl or benzyl; and $n$ is 4 or 5. The aforementioned amine reactant also serves as the solvent in this reaction. A sufficient amount of the amine is used to dissolve the acid S methyl ester, typically from about 100 to about 200 equivalents of amine reactant solvent are reacted with acid S methyl ester under nitrogen for about 1-4 days or until all of the acid S methyl ester has been consumed. The presence or absence of acid S methyl ester reactant is determined analytically during the reaction.

The cyclic and acyclic amide derivatives of acid S formed according to the process of this invention may be acetylated to determine the number of secondary hydroxyl groups present in each of the structural modifications. One equivalent of the cyclic or acyclic amide derivative of this invention is reacted with from 100 to 200 equivalents of acetic anhydride in a sufficient amount of pyridine solvent to promote the reaction. Typically, from 200 to 400 equivalents of pyridine are used. The diacetates formed indicate the presence of two hydroxyl groups in each of the cyclic and acyclic amide derivatives of acid S of this invention.

The cyclic and acyclic amide derivatives of this invention are characterized by infrared spectroscopy and, by means of their corresponding diacetates, by mass spectrometry.

The infrared spectra of the cyclic and acyclic amide derivatives of acid S of this invention are determined as thin films with an infrared absorption spectrometer equipped with a diffraction grating. In addition to providing spectral evidence for the chemical transformations of the processes of this invention, the infrared spectra of the compounds of this invention represent characteristic physical properties useful for their identification.

No useful mass spectrum of the cyclic and acyclic amide derivatives of this invention could be obtained, due to decomposition of the molecule in the mass spectrometer. However, it was possible to obtain the mass spectrum of the corresponding diacetate derivatives and to determine the molecular weight and molecular formulas for each of the amide derivatives from the mass spectrum of its diacetate.

The mass spectra of the diacetates of the cyclic and acyclic amide derivatives of acid S of this invention are measured on a double-focusing high resolution mass spectrometer utilizing a heated direct insertion probe. The molecular composition of the parent peaks are determined by employing perfluorotributylamine (mass spectral grade, available from PCR, Inc., Gainsville, Florida) as the internal standard and peak matching techniques well-known to those skilled in the art. The application of these mass spectral techniques permits not only the determination of the molecular composition of the parent ion and confirmation of the postulated transformations, but, like the aforementioned infrared measurements, provides a definitive physical property useful for identification purposes.

The novel cyclic and acyclic amide derivatives of acid S of this invention inhibit the growth of a variety of fungi, including *Histoplasma capsulatum* and *Microsporum fulvum*. Minimum inhibitory concentrations falling within the range of from 50 to 1.56 micrograms/milliliter are obtained when evaluated by the in vitro tube dilution technique described in U.S. Pat. No. 3,651,216. Thus, the compounds of the present invention are useful in the treatment of dermatophytic and systemic fungal diseases.

The novel cyclic and acyclic amide derivatives of acid S of this invention are also active against gram positive bacteria, showing minimum inhibitory concentrations in the range of 3.12 to 1.56 micrograms/milliliters against *Streptococcus pyogenes*. Thus, the compounds of the invention are useful antibacterial agents.

The novel antibacterial antifungal substances of this invention can be formulated with inert excipients into various dosage forms for oral, parenteral and topical administration by methods well-known to those skilled in the pharmacist's art. Tablets, capsules, powders, solutions, suspensions, ointments, gels and creams are included among these dosage forms.

The cyclic and acyclic amide derivatives of acid S of this invention can be administered orally, parenterally or topically to various mammals, such as dogs, cats and guinea pigs, afflicted with fungal or bacterial diseases. The effective dosage range is about 0.01 to about 100 mg/kg of body weight for the treatment of a fungal disease. For the treatment of bacterial infections, from about 0.01 to about 100 mg/kg of body weight is recommended.

The following examples are included to further illustrate the invention are not to be construed as limiting the scope of the invention:

EXAMPLE I

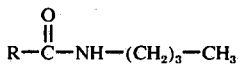

Acid S(n-butylamine)amide. A solution of acid S methyl ester (50mg) in n-butylamine (10ml) is refluxed under nitrogen for 24 hours. The excess amine is removed under reduced pressure to give an oil. The crude product is dissolved in chloroform. The chloroform solution is extracted with N hydrochloric acid, washed with water, dried over $MgSO_4$ and evaporated to give a yellow oil. The product is purified using preparative thin layer chromatography to give a yellow oil (28mg 52%). Diagnostic tlc indicates a pure homogeneous product.

Empirical formula, $C_{32}H_{51}NO_5$.
Molecular weight, 529.7.
Infrared Spectrum. $\nu$ max 3500–3200cm$^{-1}$ (OH and NH), 1670cm$^{-1}$ (C = O of amide).
Mass Spectrum. No useful mass spectrum can be obtained for this compound, but the mass spectrum of the diacetate derivative (Example VI) indicates a molecular weight of 529 and molecular formula of $C_{32}H_{51}NO_5$ for acid S (n-butylamine)amide.

EXAMPLE II

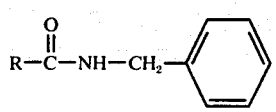

Acid S (benzylamine)amide. A solution of acid S methyl ester (50mg) in benzylamine (5ml) is heated at 110° C.–120° C. for 96 hours. The product is obtained as a yellow oil (7mg 13%) by the general method described in Example I. Diagnostic tlc indicates a pure homogeneous product.

Empirical formula, $C_{35}H_{49}NO_5$.
Molecular weight, 563.8.
Infrared Spectrum, $\nu$ max 3600–3200cm$^{-1}$ (OH and NH), 1650cm$^{-1}$ (C = O of amide).
Mass Spectrum. The mass spectrum of the diacetate derivative (Example VII) indicates a molecular weight of 563 and a molecular formula of $C_{35}H_{49}NO_5$ for acid S (benzylamine)amide.

EXAMPLE III

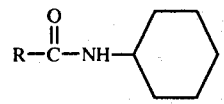

Acid S (cyclohexylamine)amide. A solution of acid S methyl ester (70mg) in cyclohexylamine (15ml) is heated at 110° C.–120° C. for 24 hours. The product is isolated as a yellow oil (11mg 14%) by the general method described in Example I. Diagnostic tlc indicates a pure homogeneous product.

Empirical formula, $C_{34}H_{53}NO_5$.
Molecular weight, 555.8.
Infrared Spectrum, $\nu$ max 3500–3200cm$^{-1}$ (OH and NH), 1640cm$^{-1}$ (C = O of amide).
Mass Spectrum. The mass spectrum of the diacetate derivative (Example VIII indicates a molecular weight of 555 and a molecular formula of $C_{34}H_{53}NO_5$ for acid S (cyclohexylamine)amide.

EXAMPLE IV

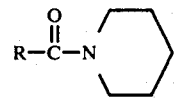

Acid S (piperidine)amide. A solution of acid S methyl ester (50mg) in piperidine (10ml) is heated at 100° C. under nitrogen for 24 hours. The product is obtained as a yellow oil (29mg 53%) by the general method described in Example I. Diagnostic tlc indicates a pure homogeneous product.

Empirical formula, $C_{33}H_{51}NO_5$.
Molecular weight, 541.8.
Infrared Spectrum, $\nu$ max 3600–3200$^{-1}$ (OH), 1630cm$^{-1}$ (C = O).
Mass Spectrum. The mass spectrum of the diacetate derivative (Example IX) indicates a molecular weight of 541 and a molecular formula of $C_{33}H_{51}NO_5$ for acid S (piperidine)amide.

EXAMPLE V

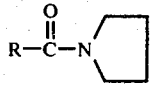

Acid S (pyrrolidine)amide. Prepared from acid S methyl ester (50mg) and pyrrolidine (10ml) by the general method described for Example I. The product is purified using preparative thin layer chromatography to give a yellow oil (10mg 18%). Diagnostic tlc indicates a pure homogeneous product.

Empirical formula, $C_{32}H_{49}NO_5$.
Molecular weight, 527.7.
Infrared Spectrum, $\nu$ max 3600–3200cm$^{-1}$ (OH), 1640cm$^{-1}$ (C = O of amide).

Mass Spectrum. The mass spectrum of the diacetate derivative (Example X) indicates a molecular weight of 527 and a molecular formula of $C_{32}H_{49}NO_5$ for acid S (pyrrolidine)amide.

EXAMPLE VI

Acid S (n-butylamine)amide diacetate. Acid S (n-butylamine)amide (50mg) is acetylated with acetic anhydride (1ml) and pyridine (2ml) at room temperature overnight. The excess acetic anhydride is decomposed with methanol. The solvents are removed under reduced pressure to give the crude product. Purification by preparative thin layer chromatography gives a pure homogeneous product as a light brown oil.

Empirical formula, $C_{36}H_{55}NO_7$.
Molecular weight, 613.8.
Infrared Spectrum, $\nu$ max 3300cm$^{-1}$ (N – H), 1745cm$^{-1}$ (C = O of acetates), 1660cm$^{-1}$ (C = O of amide).

Mass Spectrum. Molecular ion at 613 corresponding to $C_{36}H_{55}NO_7$ m/e (relative intensity) 613 (22), 595 (18), 584 (45), 554 (18), 543 (18), 518 (54), 421 (50), 300 (100) and 283 (90).

EXAMLE VII

Acid S (benzylamine)amide diacetate. Prepared from acid S (benzylamine)amide by the general procedure described in Example VI. Diagnostic tlc indicates a pure homogeneous product.

Empirical formula, $C_{39}H_{53}NO_7$.
Molecular weight, 647
Infrared Spectrum, $\nu$ max 3250cm$^{-1}$ (N – H), 1740cm$^{-1}$ (C = O of acetates) and 1640cm$^{-1}$ (C = O of amide).

| Mass Spectrum. (m−1)$^+$ ion peak matched. | |
|---|---|
| observed ion | 646 . 3677 |
| calculated for $C_{39}H_{52}NO_7$ | 646 . 3744 | m/e (relative intensity) 647 (37), 629 (20), 618 (36), 588 (8), 552 (50), 528 (12), 455 (27), 432 (10), 392 (10), 334 (28), 317 (22), 246 (34), 218 (47) and 193 (100).

EXAMPLE VIII

Acid S (cyclohexylamine)amide, diacetate. Prepared from acid S (cyclohexylamine)amide by the general procedure described in Example VI. Diagnostic tlc indicates a pure homogeneous product.

Empirical formula, $C_{38}H_{57}NO_7$.
Molecular weight, 639.8.
Infrared Spectrum, $\nu$ max 3300cm$^{-1}$ (N – H), 1740cm$^{-1}$ (C = O of acetates) and 1640cm$^{-1}$ (C = O of amide).

Mass Spectrum. Molecular ion at 639 corresponding $C_{38}H_{57}NO_7$. m/e (relative intensity) 639 (50), 621 (20), 610 (44), 579 (20), 544 (100), 519 (40), 475 (25), 447 (31) and 326 (31).

EXAMPLE IX

Acid S (piperidine)amide dicaetate. Prepared from acid S (piperidine)amide by the general procedure described in Example VI. Diagnostic tlc indicates a pure homogeneous product.

Empirical formula, $C_{37}H_{55}NO_7$.
Molecular weight, 625
Infrared Spectrum, $\nu$ max 1740cm$^{-1}$ (C = O of acetates), 1640cm$^{-1}$ (C = O of amide).

| Mass Spectrum. | |
|---|---|
| observed molecular ion | 625 . 3940 |
| calculated for $C_{37}H_{55}NO_7$ | 625 . 3978 | m/e (relative intensity) 625 (50), 607 (12), 596 (18), 566 (6), 543 (6), 530 (70), 433 (66), 370 (18), 312 (33), 224 (66), 196 (91) and 193 (100).

EXAMPLE X

Acid S (pyrrolidine)amide, diacetate. Prepared from acid S (pyrrolidine)amide by the general procedure described in Example VI. Diagnostic tlc indicates a pure homogeneous product.

Empirical formula, $C_{36}H_{53}NO_7$.
Molecular weight, 611.8.
Infrared Spectrum, $\nu$ max 1740cm$^{-1}$ (C = O of acetates) and 1640cm$^{-1}$ (C = O of amide).

Mass Spectrum. Molecular ion at 611 corresponding to $C_{36}H_{53}NO_7$. m/e (relative intensity) 611 (75), 593 (19), 582 (32), 516 (86), 419 (100) and 298 (75).

We claim:
1. The antibiotic substance, acid S (n-butylamine) amide, having the following characteristics:
Empirical formula: $C_{32}H_{51}NO_5$
Molecular weight: 529.7
Infrared Spectrum as shown in FIG. 1: $\nu$ max 3500–3200cm$^{-1}$ (OH and NH), 1670cm$^{-1}$ (C = O of amide)
Mass Spectrum of the corresponding diacetate: Molecular ion at 613 corresponding to $C_{36}H_{55}NO_7$ m/e (relative intensity) 613 (22), 595 (18), 584 (45), 554 (18), 543 (18), 518 (54), 421 (50), 300 (100) and 283 (90).

Figure 2:
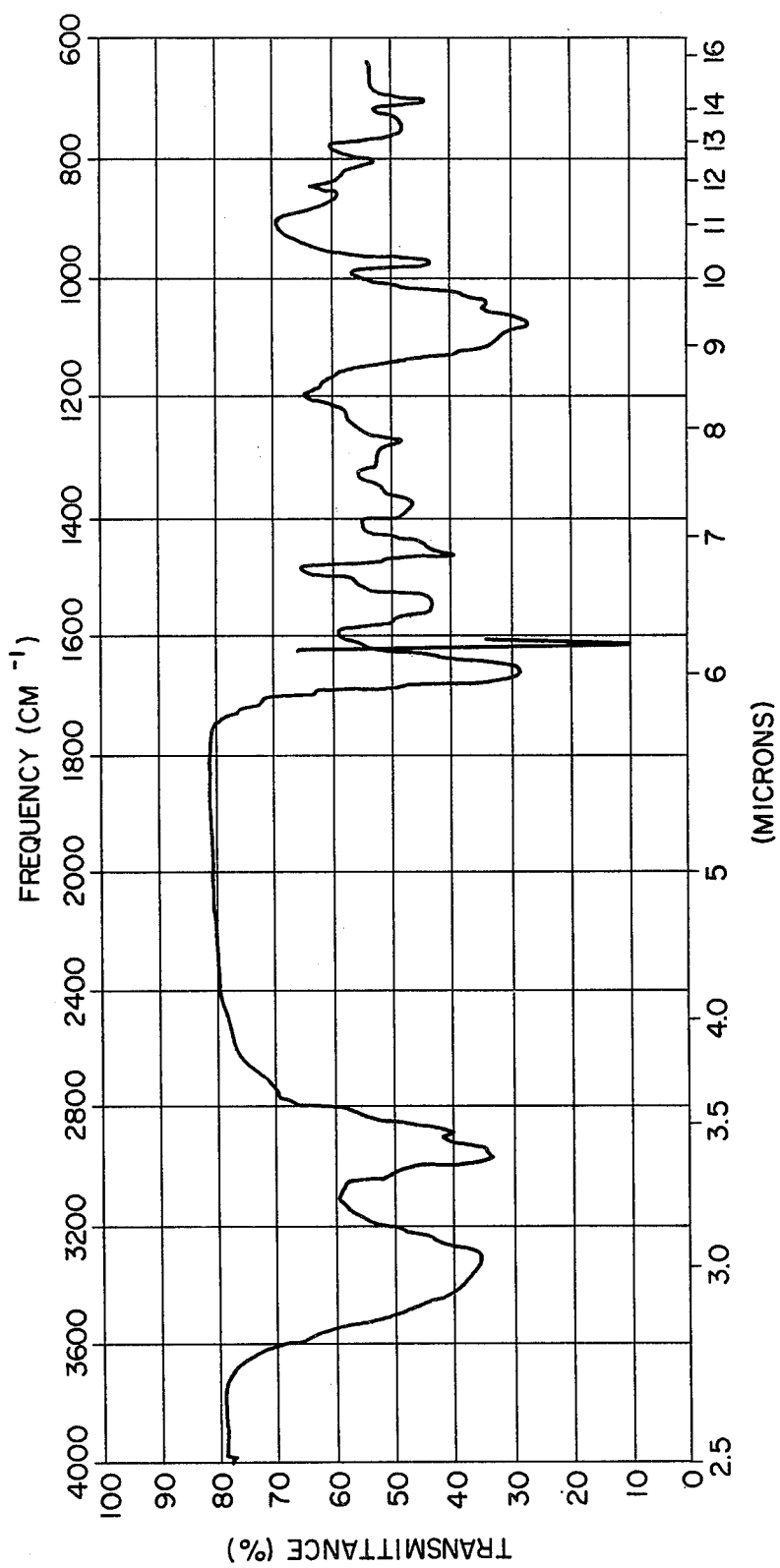
FIG. 2 depicts the infrared spectrum of acid S-(benzylamine)amide.

2. The antibiotic substance, acid S (benzylamine) amide, having the following characteristics:
Empirical formula: $C_{35}H_{49}NO_5$
Molecular weight: 563.8
Infrared Spectrum as shown in FIG. 2: $\nu$ max 3600–3200cm$^{-1}$ (OH and NH), 1650cm$^{-1}$ (C = O of amide)

| (m−1)$^+$ ion peak matched | |
|---|---|
| Observed ion | 646 . 3677 |
| calculated for $C_{39}H_{53}NO_7$ | 646 . 3744 | m/e (relative intensity) 647 (37), 629 (20), 618 (36), 588 (8), 552 (50), 528 (12), 455 (27), 432 (10), 392 (10), 334 (28), 317 (22), 246 (34), 218 (47) and 193 (100).

3. The antibiotic substance, acid S (cyclohexylamine) amide, having the following characteristics:
Empirical formula: $C_{34}H_{53}NO_5$ Molecular weight: 555.8

Figure 3:
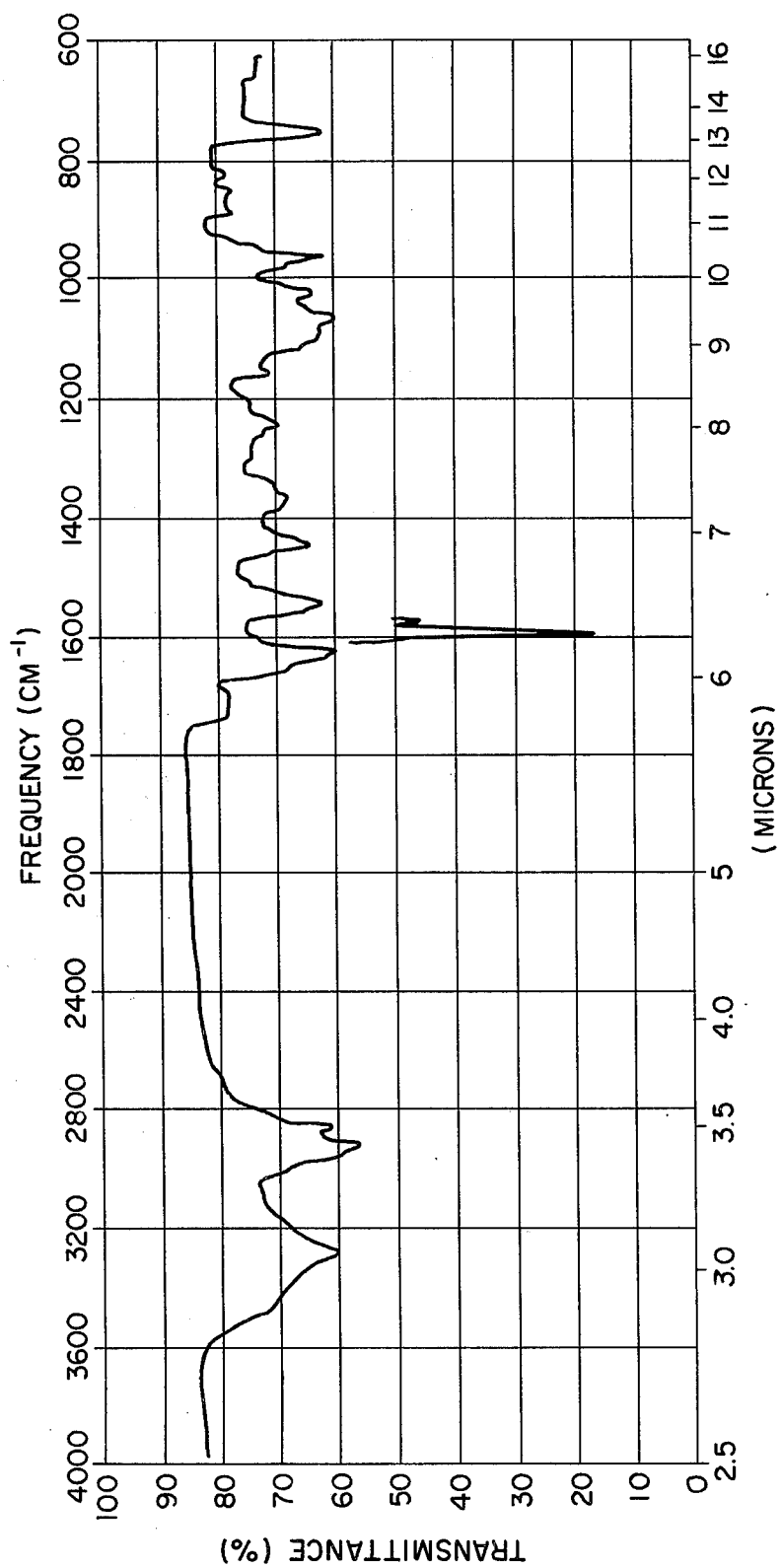
FIG. 3 depicts the infrared spectrum of acid S-(cyclohexylamine)amide.

Infrared Spectrum as shown in FIG. 3: $\nu$ max 3500–3200cm$^{-1}$ (OH and NH), 1640cm$^{-1}$ (C = O of amide)

Mass Spectrum of the corresponding diacetate: Molecular ion at 639 corresponding $C_{38}H_{57}NO_7$. m/e (relative intensity) 639 (50), 621 (20), 610 (44), 579 (20), 544 (100), 519 (40), 475 (25), 447 (31) and 326 (31).

Figure 4:
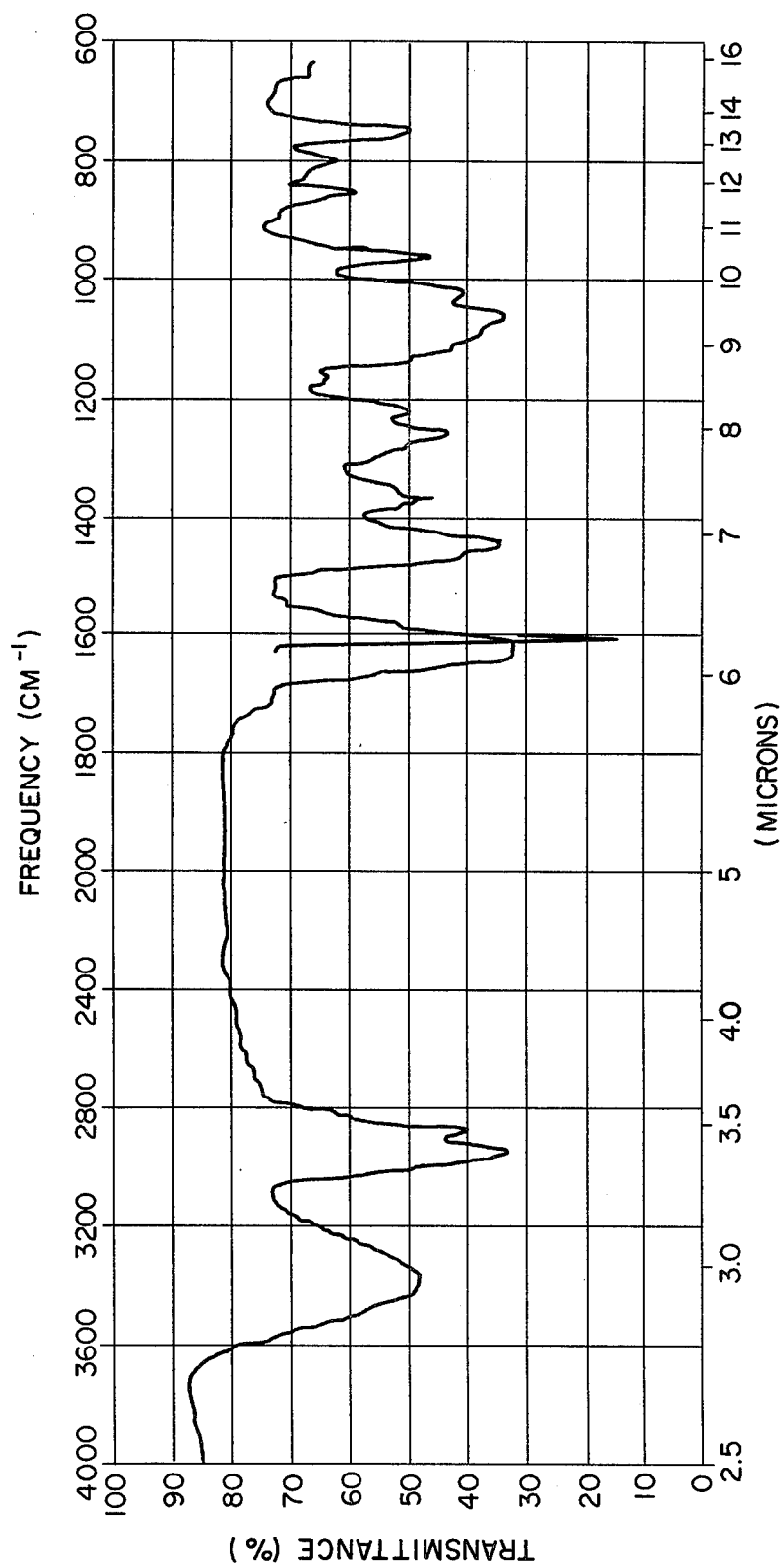
FIG. 4 depicts the infrared spectrum of acid S-(piperidine)amide.

4. The antibiotic substance, acid S (piperidine) amide, having the following characteristics:

Empirical formula: $C_{33}H_{51}NO_5$
Molecular weight: 541.8
Infrared Spectrum as shown in FIG. 4: $\nu$ max 3600–3200cm$^{-1}$ (OH), 1630cm$^{-1}$ (C = O)

| Mass Spectrum of the corresponding diacetate: | |
|---|---|
| observed molecular ion | 625 . 3940 |
| calculated for $C_{37}H_{55}NO_7$ | 625 . 3978 | m/e (relative intensity) 625 (50), 607 (12), 596 (18), 566 (6), 543 (6), 530 (70), 433 (66), 370 (18), 312 (33), 224 (66), 196 (91) and 193 (100).

Figure 5:
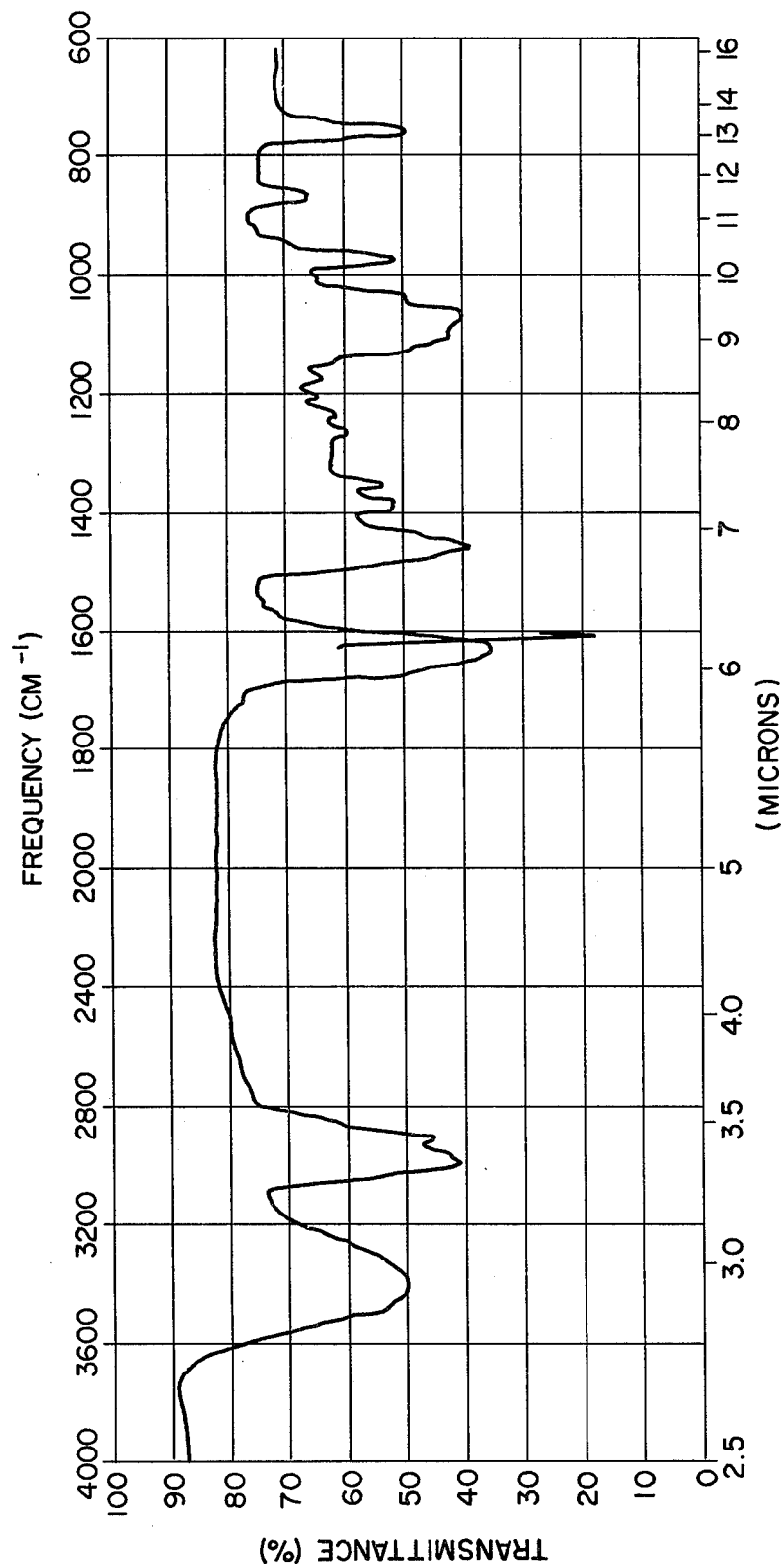
FIG. 5 depicts the infrared spectrum of acid S-(pyrrolidine)amide.

5. The antibiotic substance, acid S (pyrrolidine) amide, having the following characteristics:

Empirical formula: $C_{32}H_{49}NO_5$
Molecular weight: 537.7
Infrared Spectrum as shown in FIG. 5: $\nu$ max 3600–3200cm$^{-1}$ (OH), 1640cm$^{-1}$ (C = O of amide)

Mass Spectrum of the corresponding diacetate: Molecular ion at 611 corresponding to $C_{36}H_{53}NO_7$ m/e (relative intensity) 611 (75), 593 (19), 582 (32), 516 (86), 419 (100) and 298 (75).

* * * * *

UNITED STATES PATENT OFFICE
CERTIFICATE OF CORRECTION

PATENT NO. : 4,016,257
DATED : APRIL 5, 1977
INVENTOR(S) : DAVID T. CONNOR, SAMUEL M. RINGEL AND MAXIMILIAN VON STRANDTMANN

It is certified that error appears in the above-identified patent and that said Letters Patent are hereby corrected as shown below:

In Column 6, Claim 2, line 55, after "of amide)" insert

---Mass Spectrum of the corresponding diacetate:---.

The title reads: AMIDE DERIVATIVES OF ACIDS, AN ANTIBIOTIC PRODUCED BY POLYANGIUM CELLULOSUM VAR. FULVUM should read AMIDE DERIVATIVES OF ACID S, AN ANTIBIOTIC PRODUCED BY POLYANGIUM CELLULOSUM VAR. FULVUM Signed and Sealed this Thirteenth Day of September 1977

[SEAL]

Attest:

RUTH C. MASON
Attesting Officer

LUTRELLE F. PARKER
Acting Commissioner of Patents and Trademarks